United States Patent [19]

Okamoto

[11] 3,948,909
[45] Apr. 6, 1976

[54] ASHLESS DETERGENT DISPERSANT FOR HYDROCARBON OILS

[75] Inventor: Nobukazu Okamoto, Ohi, Japan

[73] Assignee: Toa Nenryo Kogyo Kabushiki Kaisha, Tokyo, Japan

[22] Filed: June 28, 1974

[21] Appl. No.: 483,921

[52] U.S. Cl.. 260/247.2 A; 252/51.5 A; 260/268 R; 260/482 R
[51] Int. Cl.² .................................. C07D 295/00
[58] Field of Search...... 260/482 R, 268 R, 247.2 A

[56] References Cited
UNITED STATES PATENTS

| | | | |
|---|---|---|---|
| 2,306,095 | 12/1942 | Valjavec | 260/482 R |
| 2,809,190 | 10/1957 | Kelly et al. | 260/482 R |
| 3,240,799 | 3/1966 | Hageman et al. | 260/482 R |

FOREIGN PATENTS OR APPLICATIONS

| | | | |
|---|---|---|---|
| 1,134,344 | 11/1968 | United Kingdom | 260/482 R |

*Primary Examiner*—Lorraine A. Weinberger
*Assistant Examiner*—P. J. Killos
*Attorney, Agent, or Firm*—Woodhams, Blanchard and Flynn

[57] ABSTRACT

An ashless detergent dispersant for hydrocarbon oils which comprises a mixture of ester-amide-imide compounds obtained by reacting (A) one mole of an alkenyl dibasic acid or alkenyl dibasic acid anhydride having at least 40 carbon atoms in the alkenyl moiety, with (B) 0.05 to 0.65 mole of an alkanolamine of formula $$HN(R'OH)_2$$

wherein R' is an alkylene group having 2 to 10 carbon atoms, and then reacting that resulting intermediate product, with (C) 0.1 to 0.5 mole, per mole of the alkenyl dibasic acid or alkenyl dibasic acid anhydride moiety of said intermediate product, of a member selected from the group consisting of amines of the formulae (a) $H_2N(R''NH)_nN$, (b)

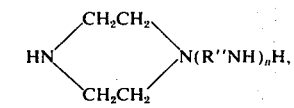

(c) 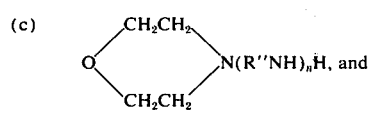 and wherein R'' is an alkylene group having 1 to 10 carbon atoms and $n$ is a number of from 1 to 6.

11 Claims, No Drawings

ASHLESS DETERGENT DISPERSANT FOR HYDROCARBON OILS

BACKGROUND OF THE INVENTION

1. Field of the Invention

This invention relates to an ashless detergent dispersant for hydrocarbon oils and to a lubricating oil composition containing said ashless detergent dispersant. More particularly, the invention relates to an ashless detergent dispersant suitable for hydrocarbon oils, which comprises a mixture of ester-amide-imide compounds obtained by reacting an alkenyl dibasic acid or alkenyl dibasic acid anhydride with an alkanolamine and with a specific amine. In greater detail, the invention relates to an ashless detergent dispersant comprising a mixture of novel compounds formed by bonding both an alkanolamine and a specific amine to an alkenyl dibasic acid or its anhydride, and to a lubricating oil composition containing a small amount of said ashless detergent dispersant.

It is a primary object of this invention to provide an ashless detergent dispersant for hydrocarbon oils having in combination a high dispersing property and a good high temperature stability and a process for preparing said ashless detergent dispersant. Another object of this invention is to provide a hydrocarbon oil composition, especially a lubricating oil composition, containing an ashless detergent dispersant having in combination a high dispersing property and a good high temperature stability.

2. Description of the Prior Art

Ashless detergent dispersants have been incorporated in petroleum products as additives for preventing or controlling formation of cold sludges owing to stop-and-go driving of vehicles and the like. Detergent dispersants of the succinimide type have been used widely for this purpose, and detergent dispersants of the hydroxybenzyl amine type have been developed as substitutes for the succinimide type dispersants. Although various ashless detergent dispersants have been proposed, most of them comprise a compound which has a polyalkylene polyamine moiety in its molecule. As ashless detergent dispersants of types other than the polyalkylene polyamine type, there have been known ashless detergent dispersants of the polyester type and the thiophosphoric acid ester type formed by employing a polyhydric alcohol.

Detergent dispersants, whether they are of the metallic type or of the ashless type, are amphoteric compounds having a combination of polar and oleophilic groups of a certain structural size in the molecule. When they are added to hydrocarbon oils, especially lubricating oils, they exhibit required activities, such as adsorbing and dispersing property, solubilizing property and acid-neutralizing property. More specifically, a detergent dispersant to be incorporated in a lubricating oil for internal combustion engines should have not only a property of adsorbing and dispersing engine sludges, but also a property of preventing sludge precursors from being oxidized or polymerized to form an oil-insoluble substance (i.e., solubilizing property). In order for an ashless detergent dispersant to fully exert its activity as an agent for preventing formation of cold sludges as pointed out above, the above solubilizing activity (antioxidative activity) is the most important and indispensable property. That is, the ashless detergent dispersant is required to function as an agent effective against sludge precursors in order to inhibit formation of sludges, rather than primarily as a dispersant for already-formed sludges.

In this connection, the above-mentioned typical commercially available additives such as the succinimide derivatives and the hydroxybenzyl amine derivatives are not fully satisfactory. The succinimide derivatives can be synthesized by reacting a polyalkenyl succinic anhydride, which is a reaction product formed by a reaction between a polyolefin and succinic anhydride, with a polyalkylene polyamine having a primary amino group. The hydroxybenzyl amine derivatives can be obtained by condensing a polyolefin-alkylated phenol, formaldehyde and a polyalkylene polyamine. Since it can be considered that each of these derivatives is a compound in which a polyolefin and a polyalkylene polyamine are bonded together through the succinimide group or the hydroxybenzyl group, they can collectively be designated by the generic term "polyolefin polyalkylene polyamine" based on their main molecular structure, although they differ in other elements introduced by the after-treatments.

Because of their effective activity in dispersing fine particles, such polyolefin polyalkylene polyamine type detergent dispersants have recently been used in diesel engine oils and the like, but for such applications they possess insufficient heat resistance. Accordingly, development of ashless detergent dispersants having an improved heat resistance, namely, a good high temperature stability, and which are effective against sludge precursors, is highly desired in the art.

The above-mentioned ashless detergent dispersants of the polyolefin polyalkylene polyamine type are insufficient as regards their high temperature stability. On the other hand, products of the ester-amide type formed by reacting a polyalkenyl maleic anhydride with diethanolamine, which were separately developed (such as those disclosed in U.S. Pat. No. 3,324,033), have a good thermal stability, but they are defective in that their dispersing property is poor. In U.S. Pat. No. 3,324,033 it is disclosed that an ashless detergent dispersant of the ester-amide type is a product obtained by reacting (1) 1 mole of an alkenyl succinic anhydride having as the alkenyl substituent a polybutene having a molecular weight of about 700 to about 1100 with (b) 0.66 to 1.5 moles, preferably 0.80 to 0.95 mole, of diethanolamine, at a temperature of 150° to 200°C. in the presence of a solvent such as xylene, in which the ester/amide ratio is from 0.5 to 1.1, preferably 0.85 to 1.0. The reaction product obtained by reaction between the polyalkenyl succinic anhydride and diethanolamine contains both ester and amino groups, and the ratio of these two groups is determined by the mixing ratio of the polyalkenyl succinic anhydride and diethanolamine and the reaction conditions, especially the reaction temperature and duration. Therefore, U.S. Pat. No. 3,324,033 teaches specific reaction conditions in order to obtain reaction products that can be used as ashless detergent dispersants for lubricating oils.

As pointed above, such ashless detergent dispersants of the ester-amide type have a better thermal stability in comparison with the known dispersants of the polyolefin polyalkylene polyamine type, but they possess an insufficient dispersing property. In contrast, ashless detergent dispersants of the succinimide type are insufficient in their thermal stability, but they have a high dispersing property. Thus, no practical additive has been developed which is sufficient in both its thermal stability and its dispersing property.

SUMMARY OF THE INVENTION

We have discovered novel ashless detergent dispersants which possess an unexpectedly improved and advantageous balance of properties, particularly a high dispersing property and a good high temperature stability, and which dispersants can be prepared by simple manufacturing steps. These novel ashless detergent dispersants can be effectively used not only for lubricating oils, but also for all other hydrocarbon oils of the mineral oil series.

More specifically, this invention provides an ashless dispersant comprising a mixture of ester-amide-imide type compounds synthesized from an alkenyl dibasic acid or anhydride thereof, an alkanolamine and an amine, and to a process for preparing such dispersants.

In accordance with one aspect of this invention, there is provided an ashless detergent dispersant comprising a mixture of compounds of the ester-amide-imide series obtained by reacting (A) 1.0 mole of an alkenyl dibasic acid or anhydride thereof having at least 40 carbon atoms in the alkenyl moiety, with (B) 0.05 to 0.65 mole, preferably 0.1 to 0.65 mole, of an alkanolamine of the formula $$HN(R'OH)_2$$

wherein R' is an alkylene group having 2 to 10 carbon atoms, and reacting that resulting intermediate, with (C) 0.1 to 0.5 mole, per one mole of the alkenyl dibasic acid or alkenyl dibasic acid anhydride moiety of said intermediate, of a member selected from the group consisting of amines of the formulae (a)   $H_2N(R''NH)_nH$, (b) 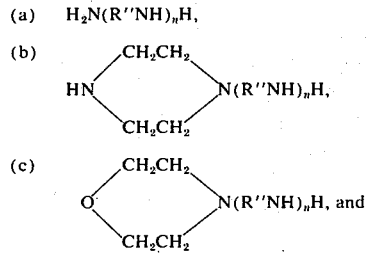

(c)

wherein R'' is an alkylene group having 1 to 10 carbon atoms and n is a number of from 1 to 6.

As is apparent from the description give hereinbelow, the "ester-amide-imide type compounds" referred to in this invention is a reaction product having a molecular structure in which both the alkanolamine and the polyalkylene polyamine are chemically bonded to the alkenyl dibasic acid or its anhydride, and it is a composition having ester, amide and imide linkages therein. This product is a very complex composition but the presence of these linkages can be confirmed by infrared absorption spectrum analysis.

In accordance with another aspect of this invention, there is provided a lubricating oil composition comprising an ashless detergent dispersant of the above-mentioned ester-amide-imide type compounds, more specifically a lubricating oil composition comprising a major amount of a lubricating oil fraction and a minor amount of said ashless detergent dispersant, according to the invention.

As described above, we have discovered, unexpectedly in view of the prior art, that the ashless detergent dispersants according to this invention possess an unexpectedly improved and advantageous balance of properties, in comparison with known ashless detergent dispersants of the ester-amide type, because the dispersants according to this invention possess a high dispersing property in combination with a good high temperature stability. More specifically, in this invention an alkenyl dibasic acid or an anhydride thereof is reacted with an alkanolamine of the formula $$HN(R'OH)_2$$

wherein R' is an alkylene group having 2 to 10 carbon atoms, to form an intermediate reaction product and that intermediate reaction product is then reacted with a member (hereinafter referred to as "polyalkylene polyamine") selected from the group consisting of amines of the formulae (a) 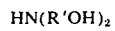  $H_2N(R''NH)_nH$, (b) 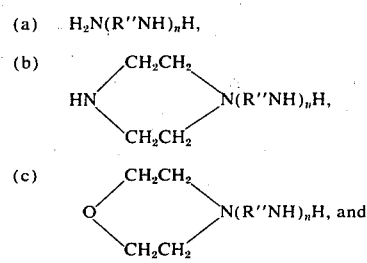

(c)

wherein R'' is an alkylene group having 1 to 10 carbon atoms, and n is a number of from 1 to 6. In short, it is critical to employ a novel mixture of compounds obtained by chemically bonding both an alkanolamine and a polyalkylene polyamine to an alkenyl dibasic acid or an anhydride thereof.

The most characteristic feature of this invention resides in that the conditions for reaction between (A) the alkenyl dibasic acid or an anhydride thereof and (B) the alkanolamine, especially the mole ratio of these two reactants, are so adjusted as to form an intermediate in which the two alcoholic hydroxyl groups in the alkanolamine molecule form ester linkages with the alkenyl dibasic acid or its anhydride and one amino group in the alkanolamine molecule forms an amide linkage with the alkenyl dibasic acid or its anhydride; and that during the subsequent reaction between this intermediate and a polyalkylene polyamine, said polyalkylene polyamine is introduced into said intermediate by formation of amide and imide linkages without releasing the alkanolamine.

In contrast, in the above-mentioned compounds of the ester-amide type, previously known as ashless detergent dispersants, all of the two hydroxyl and one amino (>N—H) groups in the secondary alkanolamine molecule are not always bonded to the alkenyl succinic anhydride. The alkenyl succinic anhydride is bifunctional to both the alcoholic hydroxyl and amino groups, and because the secondary alkanolamine has, as pointed above, two alcoholic hydroxyl and one secondary amino groups, it is considered to be trifunctional to the alkenyl succinic anhydride. Therefore, in the product obtained by reacting the alkenyl succinic anhydride with the secondary alkanolamine at a mole ratio of 1 : 0.66 to 1.5, for example, 1 : 1, according to the disclosure of U.S. Pat. No. 3,324,033, amino and hydroxyl groups are present in the free state in the resulting reaction product in a total amount of 1 mole in the specific example referred to. When this reaction product is treated with a polyalkylene polyamine, releasing of the free secondary alkanolamine caused by cleavage of the ester linkage will inevitably occur. The released secondary alkanolamine acts as a coagulant when it is copresent with various additives conventionally used in hydrocarbon oils, such as in an engine oil, thereby frequently causing clouds (suspended solids) or precipitation, with the result that the industrial properties of the lubricating oil product are degraded and its commercial value is lost.

The reaction between an ester-amide type reaction product and polyalkylene polyamine gives a very complex product and no prior art is known relating to that reaction or its reaction product. As a result of our study, however, it was confirmed that formation of imide linkages, formation of amide linkages, and molecular cutting or a cross-linking reaction resulting from the cleavage of ester linkages are simultaneously caused to occur, whereby a reaction product is formed containing a mixture of compounds having ester, amide and imide linkages. As pointed above, the released free alkanol-amine also is present in the thus-formed mixture. For example, as is seen from the following reaction formula

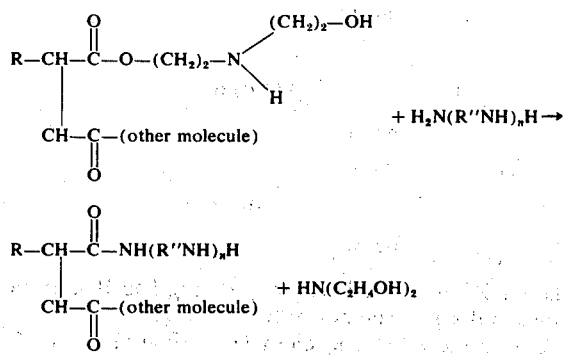

the alkanolamine bonded to the polyalkenyl succinic acid moiety only through the ester linkage is released as a consequence of the reaction with the polyalkylene polyamine. In the present invention, such releasing of the alkanolamine can be inhibited. This is due to our discovery that it is critical to react (A) 1 mole of an alkenyl dibasic acid or its anhydride such as alkenyl succinic anhydride, with (B) 0.05 to 0.65 mole, especially 0.1 to 0.65 mole, of a secondary alkanolamine, in order that the secondary alkanolamine will form two ester linkages and one amide linkage as a consequence of the reaction with the alkenyl succinic anhydride or the like. That is, it is an indispensable condition of this invention that all of the secondary amino groups of the alkanol-amine are allowed to participate in the formation of the amide linkage. If the reaction is completed under such reaction conditions, the secondary alkanolamine is bonded to at least one alkenyl dibasic acid moiety through the amide linkage, and therefore, even if the ester linkage is cleft during the subsequent reaction with the polyalkylene polyamine, the secondary alkanol amine is not released, with the result that the foregoing difficulties caused by the presence of the free alkanol-amine in the comparison process can be overcome.

The process of this invention for preparing ashless detergent dispersants comprising a mixture of ester-amide-imide type compounds by the reaction of an alkenyl dibasic acid or an anhydride thereof with an alkanolamine and a polyalkylene polyamine will now be described.

The process of this invention includes the following two reactions as basic reactions.

1. 1 mole of an alkenyl dibasic acid or an anhydride thereof, which has at least 40 carbon atoms in the alkenyl moiety, is reacted with 0.05 to 0.65 mole of an alkanolamine of the formula, $HN(R'OH)_2$, in which $R'$ is an alkylene group having 2 to 10 carbon atoms, at a reaction temperature of 100° to 250°C., to thereby form an intermediate (ester-amide).

2. The thus-formed intermediate is reacted with 0.1 to 0.5 mole, per one mole of the alkenyl dibasic acid moiety of the intermediate, of a member selected from the group consisting of amines of the formulae (a) $H_2N(R''NH)_nH$, (b) 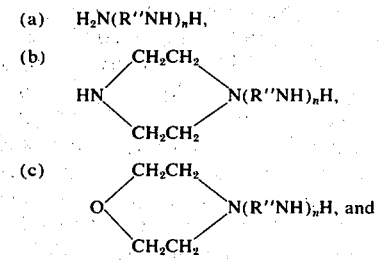

(c) (structure with O and CH₂CH₂ groups) $N(R''NH)_nH$, and wherein $R''$ is an alkylene group having 1 to 10 carbon atoms and n is a number of from 1 to 6. It is preferred to use a polyalkylene polyamine of the formula, $H_2N(R''NH)_nH$, in which $R''$ is an alkylene group having 2 to 6 carbon atoms and n is a number of from 1 to 4. This reaction is carried out at a reaction temperature of 100° to 250°C., to thereby form a mixture of ester-amide-imide type compounds.

The ashless detergent dispersant of this invention can be prepared by means of the above two-stage reaction. In this preparation process, it is possible to employ in both stages a solvent inactive in each reaction, for example, straight, branched and cyclic hydrocarbons, especially purified lubricating oil fractions. In general, it is preferred that the solvent is used in an amount almost equal to the amount of the alkenyl dibasic acid or its anhydride. In the first stage of the process, i.e. the reaction between the alkenyl dibasic acid or its anhydride and the alkanolamine, the temperature is chosen within the range of from 100° to 250°C., preferably at least 150°C. up to 250°C. As pointed out above, the product formed by this reaction comprises amides formed by reaction of the amino group with the dibasic acid moiety and esters formed by reaction of the alcoholic hydroxyl group with the dibasic acid moiety, and it also includes intramolecular/intermolecular esters and amides. It is very difficult to establish precise details of the composition and structure of such reaction product, but it is possible to confirm the presence of the ester and amide linkages by infrared absorption spectrum analysis.

The amount of the alkanolamine can be chosen in a broad range, provided that it is not more than 0.65 mole per one mole of the alkenyl dibasic acid or its anhydride. However, if the amount of the alkanolamine is very small, for example, less than 0.1 mole per one mole of the alkenyl dibasic acid or its anhydride, it is impossible to obtain a reaction product completely having the properties required of the ashless detergent dispersant of this invention. Therefore, it is preferred that the alkanolamine is used in an amount of at least 0.1 mole per one mole of the alkenyl dibasic acid or its anhydride. It must be noted, however, that products of acceptable properties for many, but not all, possible uses of the dispersant can be obtained by the use of the alkanolamine in an amount of as low as 0.05 mole of alkanolamine per one mole of the alkenyl dibasic acid or its anhydride.

Completion of the first stage reaction can be confirmed by infrared absorption spectrum analysis of the reaction product (intermediate). When a reaction vessel equipped with a mechanical agitator is employed, the reaction is generally completed in about 2 to about 5 hours. Hydrocarbons of the lubricating oil class such as mineral oils or light hydrocarbons such as xylene can be used as the reaction solvent.

The reaction of the thus-formed intermediate product with the polyalkylene polyamine is conducted at a temperature of 100° to 250°C, preferably at least 150°C. up to 250°C. The polyalkylene polyamine is employed in an amount of up to 0.5 mole per mole of the alkenyl dibasic acid moiety of the intermediate product, and from the practical viewpoint, the amount of polyalkylene polyamine is chosen within a range of from 0.1 mole to 0.5 mole per one mole of the alkenyl dibasic acid moiety of the intermediate product. Solvents such as those mentioned above may be used as the reaction solvent for this second stage reaction. When a reaction vessel equipped with a mechanical agitator is employed, the second stage reaction is completed in about 2 to about 4 hours, although the reaction time varies to some extent depending on the reaction mode.

The above reaction stages can be conducted batchwise in one reaction zone or continuously in two different reaction zones, respectively.

In the infrared absorption spectrum of the intermediate formed at the first stage, there are observed stretching vibrations ($\nu C = O$) of substantially equal intensity owing to the ester and the amide carbonyl at 1750 cm$^{-1}$ and 1640 cm$^{-1}$. In the infrared absorption spectrum of the reaction product obtained at the second stage, there are observed stretching vibrations ($\nu C = O$) owing to the imide carbonyl at 1770 cm$^{-1}$ and 1720 cm$^{-1}$, the stretching vibration ($\nu C = O$) owing to the ester carbonyl at 1750 cm$^{-1}$, and stretching vibrations ($\nu C = O$) owing to the secondary amide carbonyl and tertiary amide carbonyl, respectively, at 1680 cm$^{-1}$ and 1640 cm$^{-1}$. The intensity of the stretching vibrations of carbonyls in the above infrared absorption spectra can be changed by changing the reaction conditions, such as the mole ratio of the reactants and the reaction time, and either the degree of advance of the reaction or completion of the reaction can be established from such infrared absorption spectra.

The alkenyl dibasic acid or its anhydride used in this invention contains an alkenyl group having at least 40 carbon atoms such as a polybutenyl group, and the dibasic acid moiety is one derived from maleic anhydride, maleic acid or the like. It is especially preferred to employ an alkenyl succinic anhydride of the following formula

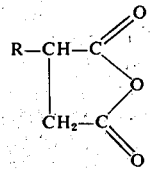

wherein R is alkenyl or halo-alkenyl having 40 to 250 carbon atoms, such as a polybutenyl succinic anhydride. Alkenyl succinic anhydrides can be prepared by reacting maleic anhydride with a polybutene, a propylene oligomer or the like at about 200°C for about 24 hours, and known preparation methods can be employed for the preparation of these alkenyl succinic anhydrides.

The alkanolamine has the formula, HN(R'OH)$_2$, wherein R' is an alkylene group having 2 to 10 carbon atoms, preferably 2 to 6 carbon atoms. Examples of the R' group are ethylene, propylene, butylene, isobutylene, pentamethylene, isopentamethylene, hexamethylene and isohexamethylene groups. Secondary alkanolamines such as diethanolamine [HN(C$_2$H$_4$OH)$_2$], di-isopropanolamine and dibutanolamine are preferably employed as the alkanolamine.

The amine used in this invention is selected from compounds of the following formulae (a) H$_2$N(R''NH)$_n$H,

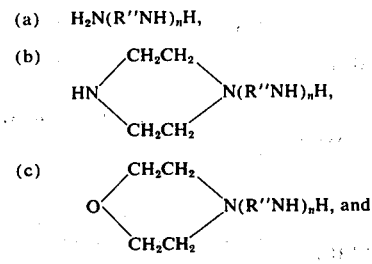

wherein R'' is an alkylene group having 1 to 10 carbon atoms and $n$ is a number of from 1 to 6.

Among these amines, diethylene triamine, triethylene tetramine, tetraethylene pentamine and the like are preferred. Further, piperazine derivatives such as β-aminoethyl piperazine, β-aminopropyl piperazine, morpholine derivatives such as β-aminobutyl morpholine, etc., and ethyl amine, n-butyl amine, dodecyl amines and the like can be used.

The ashless detergent dispersant of this invention can improve the properties of hydrocarbon oils, for example, gasolines, middle oils and heavy oil fractions such as lubricating oils, especially engine oils, transmission oils and other industrial lubricating oils, when it is incorporated into such hydrocarbon oils.

The lubricating oil composition of this invention comprises a major amount of a lubricating oil fraction and a minor amount of the above ashless detergent dispersant. The ashless detergent dispersant is incorporated in an amount of 0.1 to 30 percent by weight, preferably 1 to 10 percent by weight, based on the total weight of the lubricating oil composition.

The kind of lubricating oil fraction employed is not critical, and petroleum hydrocarbon fractions having a boiling point higher than about 300°C. prepared from crude oil through distillation under atmospheric or reduced pressure, solvent extraction and purification such as hydrogenation or adsorption are usually employed. Preferred fractions or cuts are chosen appropriately depending on the requirements or standards for the particular use to be made of the lubricating oil composition, in accordance with conventional practice.

More specifically, liquid hydrocarbon oils having, as the lubricating viscosity, a kinematic viscosity of about 2 to 1000 centistokes (at 97.8°C.) are preferably employed as the lubricating oil fraction. For example, there are employed hydrocarbon fractions such as lubricating oils for internal combustion engines for land and marine uses specified by the Japanese Industrial Standards (JIS K 2216 and JIS K 2215), transmission oils, gear oils and other industrial lubricating oils. The ashless detergent dispersant of this invention does not inhibit the activities of other additives usually incorporated into lubricating oil compositions, such as anti-oxidants, pour point depressants, viscosity index improvers and the like and the lubricating oil compositions of this invention can include such additives in accordance with conventional practice.

For example, in the lubricating oil composition of this invention, a metal dialkyl dithiophosphate (such as zinc dialkyl dithiophosphate and barium dialkyl dithiophosphate) can be used in an amount of about 0.1 to 5 percent by weight as an antioxidant, and as the viscosity index improver there can be employed polymethacrylic acid salts, olefin copolymers (such as ethylene-propylene copolymer) and the like. Further, an alkaline earth metal alkyl phenoxide (such as barium dodecyl cresylate, calcium dodecyl phenoxide and barium nonyl phenoxide) can be used in an amount of about 0.1 to about 5 percent by weight as a metallic detergent dispersant.

The ashless detergent dispersant of this invention exhibits unexpectedly improved effects as shown hereinbelow in the Examples when it is used with hydrocarbon oils of the mineral oil series, but it can be effectively used also for synthetic lubricating oils of the ester, polyphenyl ether or polyolefin type.

EXAMPLE 1

A 500 ml capacity, round-bottom, three-neck flask was charged with 300 g of polybutene (having an average molecular weight of 1080) and 40 g of maleic anhydride, and the mixture was heated at about 200°C. under agitation for 24 hours. The reaction mixture was allowed to cool, and then 500 ml of n-hexane was added thereto, and the mixture was filtered. Then, the n-hexane was distilled off by means of a rotary evaporator. The resulting red transparent residue was heated at 200°C. under reduced pressure (0.2 mm Hg) to remove unreacted maleic anhydride and the remaining trace of n-hexane. The saponification number of the thus-prepared polybutenyl succinic anhydride was 105 KOH mg/g. Then, 7 g of diethanolamine and 120 g of mineral oil (neutralization number = 150; viscosity index = 110) were added to 118 g (0.1 mole) of the thus-obtained polybutenyl succinic anhydride, and the mixture was heated at 170° to 180°C. for 2 hours, during which time nitrogen was introduced into the reaction vessel and the mixture was agitated. Water formed by the reaction was removed from the reaction system. In the infrared absorption spectrum of the intermediate product thereby obtained there were observed the stretching vibration ($\nu C = O$) owing to the ester at 1150 cm$^{-1}$ and the stretching vibration ($\nu C = O$) owing to the amide at 1640 cm$^{-1}$. After the reaction had been continued in the above manner for 2 hours, 9.45 g of tetraethylene pentamine was added to the reaction mixture and heating was further continued under agitation. In the infrared absorption spectrum of the final product obtained by conducting the second stage reaction in this manner for 1 hour, there were observed stretching vibrations ($\nu C = O$) owing to the imide at 1770 cm$^{-1}$ and 1720 cm$^{-1}$, the stretching vibration ($\nu C = O$) owing to the ester at 1750 cm$^{-1}$, and stretching vibrations ($\nu C = O$) owing to the amide at 1680 cm$^{-1}$ and 1640 cm$^{-1}$.

EXAMPLE 2

A 300 ml capacity, round-bottom, three-neck flask was charged with 118 g (0.1 mole) of the same polybutenyl succinic anhydride as prepared in Example 1, 5 g of diethanolamine and 120 g of mineral oil (neutralization number = 150; viscosity index = 110), and the mixture was heated at 200°C. for 2 hours under agitation while introducing nitrogen into the reaction vessel. To the thus-obtained reaction product there was added 7.6 g of tetraethylene pentamine, and heating was further continued under agitation for 1 hour. The resulting final product was a red transparent viscous liquid.

EXAMPLE 3

In the same manner as in Example 2, 118 g (0.1 mole) of the same polybutenyl succinic anhydride as prepared in Example 1, 2.7 g of di-isopropanolamine and 120 g of mineral oil (neutralization number = 150; viscosity index = 110) were heated at 200°C in a nitrogen atmosphere. After the heating was continued for 2 hours, 5.8 g of N-aminoethyl piperazine was added to the reaction mixture, and heating was further continued for 1 hour under agitation to obtain a red transparent viscous liquid as the final product.

EXAMPLE 4

A 3 l capacity, round-bottom, three-neck flask was charged with 700 g (0.59 mole) of the same polybutenyl succinic anhydride as prepared in Example 1, 30 g of diethanolamine and 700 g of mineral oil (neutralization number = 150; viscosity index = 110), and the mixture was heated at 170°C. under agitation for 2 hours, during which time nitrogen was bubbled through the reaction mixture and the water formed by the reaction was removed from the reaction system. To the resulting reaction mixture was added 55 g of tetraethylene pentamine, and heating was further continued for 1 hour. The infrared absorption spectrum of the thus-obtained final product was the same as that of the final product obtained in Example 1.

EXAMPLE 5

The properties of the ester-amide-imide type ashless detergent dispersant obtained as described in Example 4 were evaluated by the following test.

The engine oil tested was a multigrade oil (10/W-30 grade) containing 1.8 wt. percent of the ashless detergent dispersant of Example 4, 1.0 wt. percent of zinc dialkyl dithiophosphate, 4.0 wt. percent of a viscosity index improver, and prescribed amounts of a pour point depressant, a defoaming agent and a metallic detergent dispersant. The basic oil used was a solvent extraction oil comprising 80 percent by volume of a fraction having a neutralization number of 150 and a viscosity index of 110 and 20 percent by volume of a fraction having a neutralization number of 500 and a viscosity index of 100. The engine test was conducted according to the Toyota MS test method. The test procedures and conditions are set forth in Table 1, and the results of the test are shown in Table 2. From these results it is seen that the sample containing the ashless detergent dispersant of this invention prepared in Example 4 was superior in both the piston varnish results and the varnish average results with respect to control samples of the same engine oil, except that the control samples contained as dispersants commercially available succinimide and the ester-amide compound synthesized according to U.S. Pat. No. 3,324,033, respectively.

Table 1

Toyota MS Engine Test Method*

| Engine Tested : | Toyota New 5R model engine, water-cooled, parallel 4 cylinders, 2000 cc, closed type PCV valve equipped | | |
|---|---|---|---|
| Operation Conditions : | | | |
| State | I | II | III |
| Time | 45 minutes | 2 hours | 75 minutes |
| Engine Speed (rpm) | 600 | 2500 | 2500 |
| Load (PS) | — | 34 | 34 |
| Oil Temperature (°C) | 50 | 80 | 100 |
| Water Temperature (°C) | 45 | 50 | 80 |
| Cycle Number | | 48 | |
| Stoppage | 8 hours after every 4 cycles' operation | | |
| Total Operation Time (hr) | | 192 | |

*Hiroshi Minamitani, "Junkatsu" (Lubrication), 17, 259 (1972)

Table 2

Results of Toyota MS Engine Test
(full mark of 10 points)

| | Succinimide* | Ester-Amide** | Product of Example 4 |
|---|---|---|---|
| Sludge Average | 9.6 | 9.5 | 9.6 |
| Piston Varnish | 7.9 | 7.8 | 9.2 |
| Varnish Average | 8.4 | 8.1 | 9.1 |

*commercially available product
**synthesized product of Patent No. 3 324 033

The embodiments of the invention in which an exclusive property or privilege is claimed are defined as follows:

1. An ashless detergent dispersant composition consisting essentially of a reaction product obtained by a two stage reaction in which, in the first stage, (A) alkenyl dicarboxylic acid or alkenyl dicarboxylic acid anhydride, wherein the alkenyl has at least 40 carbon atoms, is reacted with (B) an alkanolamine of the formula $HN(R'OH)_2$, wherein $R'$ is alkylene having 2 to 10 carbon atoms, at a molar ratio of (A):(B) in the range of from 1:0.05 to 1:0.65, to form an intermediate; and, in the second stage, said intermediate is reacted with (C) a member selected from the group consisting of amines of the formulae

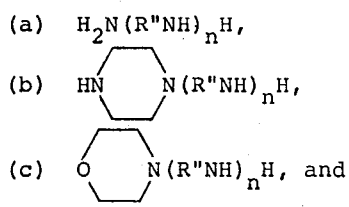

wherein $R''$ is alkylene having 1 to 10 carbon atoms and $n$ is an integer of from 1 to 6, at a molar ratio of (alkenyl dicarboxylic acid or alkenyl dicarboxylic acid anhydride moiety in said intermediate) :C in the range of from 1:0.1 to 1:0.5, to obtain a reaction product containing ester, amide and imide linkages.

2. An ashless detergent dispersant composition according to claim 1, in which the molar ratio of (A):(B) is in the range of from 1:0.10 to 1:0.65.

3. An ashless detergent dispersant composition according to claim 1, in which the reaction temperatures in both stages are in the range of 100° to 250°C.

4. An ashless detergent dispersant composition according to claim 1, in which the alkenyl has a molecular weight of about 600 to about 1500.

5. An ashless detergent dispersant composition according to claim 1, in which (A) is a polybutenyl succinic anhydride obtained by reacting polybutene with maleic anhydride.

6. An ashless detergent dispersant composition according to claim 1, in which (B) is selected from the group consisting of diethanolamine, diisopropanolamine and dibutanolamine.

7. An ashless detergent dispersant composition according to claim 1, in which (C) is selected from the group consisting of diethylene triamine, triethylene tetramine and tetraethylene pentamine.

8. An ashless detergent dispersant composition according to claim 1, in which (C) is selected from the group consisting of β-aminoethyl piperazine and β-aminopropyl piperazine.

9. An ashless detergent dispersant composition according to claim 1, in which (C) is β-aminobutyl morpholine.

10. An ashless detergent dispersant composition according to claim 1, in which (C) is selected from the group consisting of ethylamine, n-butylamine and dodecylamine.

11. A process for synthesizing an ashless detergent dispersant composition which comprises:
reacting in a first stage at 100° to 250°C., (A) alkenyl dicarboxylic acid or alkenyl dicarboxylic acid anhydride, wherein the alkenyl has at least 40 carbon atoms, with (B) an alkanolamine of the formula HN(R'OH)₂, wherein R' is alkylene having 2 to 10 carbon atoms, at a molar ratio of (A):(B) in the range of from 1:0.05 to 1:0.65, to form an intermediate;

and, reacting in a second stage, at 100° to 250°C., said intermediate with (C) a member selected from the group consisting of amines of the formulae (a) 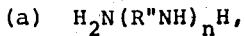 H₂N(R"NH)ₙH, (b) 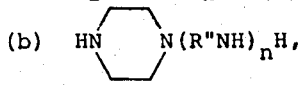 HN⟩N(R"NH)ₙH, (c) 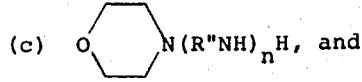 O⟩N(R"NH)ₙH, and wherein
R" is alkylene having 1 to 10 carbon atoms and
n is an integer of from 1 to 6, at a molar ratio of (alkenyl dicarboxylic acid or alkenyl dicarboxylic acid anhydride moiety in said intermediate) :C in the range of from 1:0.1 to 1:0.5.

* * * * *